United States Patent [19]
Achter et al.

[11] Patent Number: 5,883,231
[45] Date of Patent: Mar. 16, 1999

[54] ARTIFICIAL MENSES FLUID

[75] Inventors: Amy Michele Achter, Neenah, Wis.; Crystal Sutphin Leach, Atlanta; Jack Nelson Lindon, Alpharetta, both of Ga.; Heather Anne Sorebo, Appleton, Wis.; Mary Garvie Weber, Alpharetta, Ga.

[73] Assignee: Kimberly-Clark Worldwide, Inc., Neenah, Wis.

[21] Appl. No.: 916,993

[22] Filed: Aug. 21, 1997

Related U.S. Application Data

[60] Provisional application No. 60/046,702. May 14, 1997.

[51] Int. Cl.⁶ .............................. A61K 35/14; C07K 1/00; A23J 1/00
[52] U.S. Cl. .................... 530/362; 530/359; 530/366; 530/367; 530/380; 530/412; 530/418; 530/422; 424/529; 424/530; 424/533; 424/581
[58] Field of Search .............................. 530/362, 359, 530/366, 367, 380, 412, 418, 422, 829, 830, 827; 424/529, 530, 533, 581

[56] References Cited

U.S. PATENT DOCUMENTS

| | | | |
|---|---|---|---|
| 3,338,992 | 8/1967 | Kinney | 264/24 |
| 3,341,394 | 9/1967 | Kinney | 161/72 |
| 3,502,763 | 3/1970 | Hartman | 264/210 |
| 3,542,615 | 11/1970 | Dobo et al. | 156/181 |
| 3,546,319 | 12/1970 | Prevorsek | 260/857 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 4,100,324 | 7/1978 | Anderson et al. | 428/288 |
| 4,321,924 | 3/1982 | Ahr | 128/287 |
| 4,340,563 | 7/1982 | Appel et al. | 264/518 |
| 4,795,668 | 1/1989 | Krueger et al. | 428/174 |
| 4,818,464 | 4/1989 | Lau | 264/510 |
| 5,057,368 | 10/1991 | Largman et al. | 428/397 |
| 5,069,970 | 12/1991 | Largman et al. | 428/373 |
| 5,108,820 | 4/1992 | Kaneko et al. | 428/198 |
| 5,108,827 | 4/1992 | Gessner | 428/219 |
| 5,200,248 | 4/1993 | Thompson et al. | 428/131 |
| 5,277,976 | 1/1994 | Hogle et al. | 428/397 |
| 5,294,482 | 3/1994 | Gessner | 428/287 |
| 5,336,552 | 8/1994 | Strack et al. | 428/224 |
| 5,356,626 | 10/1994 | Yeo et al. | 424/195.1 |
| 5,382,400 | 1/1995 | Pike et al. | 264/168 |
| 5,466,232 | 11/1995 | Cadieux et al. | 604/378 |
| 5,466,410 | 11/1995 | Hills | 264/172.11 |
| 5,540,992 | 7/1996 | Marcher et al. | 428/373 |
| 5,549,589 | 8/1996 | Horney et al. | 604/366 |

OTHER PUBLICATIONS

John A. Manson and Leslie H. Sperling "Polymer Blends and Composites," Plenum Press, 1976, pp. 273–277.

The Textile and Research Journal, vol. 37, 1967, p. 356 and Chatterjee's Absorbency, Elsevier Scenic Publishers, B.V. 1985, pp. 36–40.

*Primary Examiner*—Cecilia J. Tsang
*Assistant Examiner*—Abdel A. Mohamed
*Attorney, Agent, or Firm*—James B. Robinson

[57] ABSTRACT

There is provided a bodily fluid simulant made from red blood cells in an amount between about 10 and about 60 weight percent, egg white in an amount between 20 and 50 weight percent, and plasma.

12 Claims, No Drawings

ARTIFICIAL MENSES FLUID

This application claims priority from US Provisional Application no. 60/046,702 filed May 14, 1997.

BACKGROUND OF THE INVENTION

The field of personal care products includes diapers, training pants, adult incontinence articles and feminine hygiene products like tampons and sanitary napkins, also called pads. In the course of development of such products, it is useful, indeed almost a requisite, that such items be tested to determine how well they function in use. Such testing may be done by a "use test" in which people wear the item to be tested for a finite time and return the used item for evaluation, usually also giving their opinion of the item. Use testing is, however, a rather tedious and time consuming exercise and so is usually reserved for the products most likely to be commercialized or closest to commercialization. The examination of items tested with genuine body fluids also exposes the researcher to any viruses or diseases which may be present therein. Moreover, for feminine hygiene applications, genuine menses fluid is a highly variable substance which has a great range of viscosity and other properties differing from woman to woman and even over short time periods in each woman, making testing with actual menses fluid somewhat problematical.

As a result of this concern for safety, cost and variability, a number of artificial body exudates have been developed. One such fluid is an artificial feces (BM) used in the testing diapers and the like, which is described in detail in U.S. Pat. No. 5,356,626, commonly assigned. Another such fluid is known as "Z-Date", available from PPG Industries, Inc. of Pittsburgh, Penn., which is an artificial menses consisting of water, red dye, and a thickener. Yet another artificial menses fluid is mentioned in U.S. Pat. No. 4,321,924, incorporated herein by reference in its entirety, at column 7, lines 51–60.

Previous menses simulants, though useful, have proven unsatisfactory in the emulation of many properties of actual menses. Features such as viscosity, cell size, debris content and others have not been provided to the degree necessary for the reliable testing of today's highly engineered, high performance products. There remains, therefore, a need for an artificial menses fluid which more closely mimics actual menses fluid yet which is safe to use, consistent in properties, and cost effective, and it is an object of this invention to provide such a fluid.

SUMMARY OF THE INVENTION

The objects of this invention are achieved by a bodily fluid simulant made from red blood cells in an amount between about 10 and about 60 weight percent, egg white in an amount between 20 and 50 weight percent, and plasma.

DETAILED DESCRIPTION

The artificial menses of this invention may be made from blood and egg white by separating the blood into plasma and red cells and separating the white into thick and thin portions, where "thick" means it has a viscosity after homogenization above about 20 centipoise at 150 $sec^{-1}$, combining the thick egg white with the plasma and thoroughly mixing, and finally adding the red cells and again thoroughly mixing. It should be noted that the blood must be treated in some manner so that it may be processed without coagulating. Various methods are known to those skilled in the art, such as defibrinating the blood to remove the clotting fibrous materials, the addition or anti-coagulant chemicals and others. The blood must be non-coagulating in order to be useful in this invention and any method which accomplishes this without damaging the plasma and red cells is acceptable.

More particularly, one example of an artificial menses fluid may be prepared as follows:

Blood, in this example defibrinated swine blood, was separated by centrifugation at 3000 rpm for 30 minutes, though other methods or speeds and times may be used if effective. The plasma was separated and stored separately, the buffy coat removed and discarded and the packed red blood cells stored separately as well.

Eggs, in this example jumbo chicken eggs, were separated, the yolk and chalazae discarded and the egg white retained. The egg white was separated into thick and thin portions by straining the white through a 1000 micron nylon mesh for about 3 minutes, and the thinner portion discarded. Note that alternative mesh sizes may be used and the time or method may be varied provided the viscosity is at least that required. The thick portion of egg white which was retained on the mesh was collected and drawn into a 60 cc syringe which was then placed on a programmable syringe pump and homogenized by expelling and refilling the contents five times. In this example, the amount of homogenization was controlled by the syringe pump rate of about 100 ml/min, and the tubing inside diameter of about 0.12 inches. After homogenizing the thick egg white had a viscosity of about 20 centipoise at 150 $sec^{-1}$ and was then placed in the centrifuge and spun to remove -debris and air bubbles at about 3000 rpm for about 10 minutes, though any effective method to remove debris and bubbles may be used.

After centrifuging, the thick, homogenized egg white, which contains ovamucin, was added to a 300 cc FENWAL® TRANSFER PACK® container using a syringe. Then 60 cc of the swine plasma was added to the Transfer Pack® container. The Transfer Pack was clamped, all air bubbles removed, and placed in a Stomacher lab blender where it was blended at normal (or medium) speed for about 2 minutes. The Transfer Pack® container was then removed from the blender, 60 cc of swine red blood cells were added, and the contents mixed by hand kneading for about 2 minutes or until the contents appeared homogenous. A hematocrit of the final mixture showed a red blood cell content of about 30 weight percent and generally should be at least within a range of 28–32 weight percent for artificial menses made according to this example. The amount of egg white was about 40 weight percent.

The ingredients and equipment used in the preparation of artificial menses are readily available. Below is a listing of sources for the items used in the example, though of course other sources may be used providing they are approximately equivalent.

Blood (swine): Cocalico Biologicals, Inc., 449 Stevens Rd., Reamstown, Pa. 17567, (717) 336–1990.

FENWAL® TRANSFER PACK® container, 300 ml, with coupler, code 4R2014: Baxter Healthcare Corporation, Fenwal Division, Deerfield, Ill. 60015.

Harvard Apparatus Programmable Syringe Pump model no. 55–4143: Harvard Apparatus, South Natick, Mass. 01760.

Stomacher 400 laboratory blender model no. BA 7021, serial no. 31968: Seward Medical, London, England, UK.

1000 micron mesh, item no CMN-1000-B: Small Parts, Inc., PO Box4650,Miami Lakes, Fla. 33014–0650, 1-800-220-4242.

Hemata Stat-II device to measure hemocrits, serial no.1194Z03127: Separation Technology, Inc., 1096 Rainer Drive, Altamont Springs, Fla. 32714.

It is important to note that though only one example of an artificial menses fluid is given herein, the inventors have found that a range of ingredients and preparation conditions may be used to produce menses with properties varying from the example and useable for testing. The inventors have found that the amount of red blood cells may be between about 10 and 60 weight percent or more particularly between about 25 and 40 weight percent. The egg white may be between about 20 and 50 weight percent or more particularly between about 20 and 40 weight percent. The balance may be plasma and, for example, an ingredient to simulate particulates. The resulting fluid is useable for testing as an artificial menses fluid. Likewise the inventors have found that the preparation conditions may be varied by for example, centrifuging the ingredients at different speeds for different amounts of time from that shown in the example or straining the egg whites under different conditions, Furthermore, the ingredients may be varied, for example, by using bovine blood or human blood or by using eggs from other than chickens. Any of these changes are intended to be within the scope of the invention and are a means of providing particular menses simulants which have specifically desired properties for various types of testing and product development. The artificial menses of this invention mimics the rheological and biochemical properties of genuine menses fluid.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A bodily fluid simulant comprising red blood cells in an amount between about 10 and about 60 weight percent, bird egg white in an amount between 20 and 50 weight percent, and plasma in an amount up to 70 weight percent.

2. The fluid of claim 1 wherein said egg white is that portion of egg white having a viscosity after homogenization greater than about 20 centipoise at $150 \sec^{sec-1}$.

3. The fluid of claim 1 wherein said blood plasma and red blood cells are from swine blood which has been centrifuged to separate said blood plasma and red blood cells.

4. The fluid of claim 1 wherein said egg white and blood plasma are mixed prior to the addition of said red blood cells.

5. The fluid of claim 1 wherein said fluid is applied to a feminine hygiene product.

6. The fluid of claim 1 where said red blood cells are present in an amount between about 25 and 40 weight percent.

7. The fluid of claim 1 wherein said egg white is present in an amount between about 20 and 40 weight percent.

8. The fluid of claim 1 having a hematocrit of about 28 to about 32 percent.

9. The fluid of claim 1 wherein said red blood cells are present in an amount of about 30 weight percent and said egg white is present in an amount of about 40 percent.

10. A process of making a body fluid simulant comprising the steps of:

separating blood into plasma, buffy coat and red blood cell portions and discarding said buffy coat portion;

straining egg white to produce a thick portion and a thin portion and retaining said thick portion;

infusing said egg white thick portion;

centrifuging said egg white thick portion to remove debris and air bubbles;

adding said plasma to said egg white thick portion and mixing thoroughly;

adding said red blood cells to said thoroughly mixed plasma and egg white thick portion and mixing thoroughly.

11. The process of making a fluid of claim 10 whereby said blood is separated by centrifuging.

12. The process of making a fluid of claim 10 whereby said plasma and egg white thick portion are mixed thoroughly by blending.

* * * * *

UNITED STATES PATENT AND TRADEMARK OFFICE
CERTIFICATE OF CORRECTION

PATENT NO. : 5,883,231
DATED : March 16, 1999
INVENTOR(S) : Amy M. Achter et al.

It is certified that error appears in the above-identified patent and that said Letters Patent is hereby corrected as shown below:

Column 1, Line 30, "testing diapers" should read --testing of diapers--

Column 2, Line 29, "-debris" should read --debris--

Column 4, Line 8, "150 sec$^{sec-1}$." of Claim 2 should read --150 sec$^{-1}$.--

Signed and Sealed this

Twentieth Day of July, 1999

Attest:

Attesting Officer

Q. TODD DICKINSON

Acting Commissioner of Patents and Trademarks